US00PP23785P3

(12) United States Plant Patent
LaBonte et al.

(10) Patent No.: US PP23,785 P3
(45) Date of Patent: Jul. 30, 2013

(54) SWEETPOTATO PLANT NAMED '07-146'

(50) Latin Name: ***Ipomoea batatas* (L.)**
Varietal Denomination: 07-146

(75) Inventors: Don R. LaBonte, Baton Rouge, LA (US); Arthur Q. Villordon, Monroe, LA (US); Tara Smith, Chase, LA (US); Christopher A. Clark, Baton Rouge, LA (US)

(73) Assignee: Board of Supervisors of Louisiana State University and Agricultural and Mechanical College Through The LSU AgCenter, Baton Rouge, LA (US)

( * ) Notice: Subject to any disclaimer, the term of this patent is extended or adjusted under 35 U.S.C. 154(b) by 0 days.

(21) Appl. No.: 13/373,631

(22) Filed: Nov. 22, 2011

(65) Prior Publication Data

US 2013/0133119 P1 May 23, 2013

(51) Int. Cl.
*A01H 5/00* (2006.01)

(52) U.S. Cl.
USPC ..... Plt./258

(58) Field of Classification Search
USPC ..... Plt./258
See application file for complete search history.

*Primary Examiner* — Annette Para
(74) *Attorney, Agent, or Firm* — James C. Carver

(57) ABSTRACT

A new variety of sweetpotato identified as '07-146' is disclosed having disease resistance to *fusarium* wilt, *rhizopus* soft rot, and *Streptomyces* soil rot, an orange flesh, and high yield characteristics.

3 Drawing Sheets

The development of this invention was partially funded by the Government through a grant for the United States Department of Agriculture, USDA NIFA Grant Number NA/LAB93957. The Government may have certain rights in this invention.

This invention pertains to a new and distinct variety of sweetpotato.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

Genus And Species Name

This new and distinct sweetpotato variety, *Ipomoea batatas* (L.) Lam., demonstrates superior disease resistance to *Fusarium* wilt, soil rot, and *Rhizopus* soft rot and exhibits an orange flesh. It also demonstrates high yield characteristics in comparison to 'Beauregard'.

Variety Denomination

This new and distinct sweetpotato variety is identified as '07-146', and is characterized by a red skin, orange flesh, high yield, and elevated sucrose content.

BRIEF DESCRIPTION OF THE DRAWINGS

The file of this patent contains at least one photograph executed in color. Copies of this patent or patent application with color drawing(s) will be provided by the Patent and Trademark Office upon request and payment of the necessary fee.

DETAILED BOTANICAL DESCRIPTION

Observations of this new variety of sweetpotato, named '07-146', were made approximately 90-110 days after planting. This new variety of sweetpotato, named '07-146', resulted from an open pollinated cross performed in 2006 to the female parent '89-110' (not patented). The male parent was unknown. Four patented male parents ('L96-117' (U.S. Plant Pat. No. 15,038 P2); 'Bienville' (U.S. Plant Pat. No. 15,380 P3); 'Evangeline' (U.S. Plant Pat. No. 19,710 P3); and 'Murasaki-29' (U.S. Plant Pat. No. 19,955 P2) were among the potential pollen sources in the crossing nursery. '07-146' was developed to provide a variety with characteristics similar to 'Beauregard' (unpatented), but with improved yield and higher sucrose content.

Plants of '07-146' and 'Beauregard' are different. A red [2.5 R (red)] marking at the base of the leaf junction with the petiole is larger in comparison to a similar marking found on 'Beauregard' and extends the length of the adaxial veins of mature leaves and was present throughout major adaxial veins in immature leaves. 'Beauregard' has no red hue to veins. Color terminology used herein is in accordance with the MUNSELL® Book of Color (Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety '07-146'.

'07-146' roots were stored during the winter at Chase, La. '07-146' was planted the following spring, resulting in approximately 8-10 sprouts per root. Cuttings from the sprouts were transplanted successfully for asexual reproduction. Asexual propagation of the new cultivar by cuttings has shown that the unique features of this new sweetpotato were stable, and that the plant reproduced true to type in successive generations of asexual propagation. Plants described herein were approximately 90-110 days in age from planting in full sun field plantings.

Figure 1:
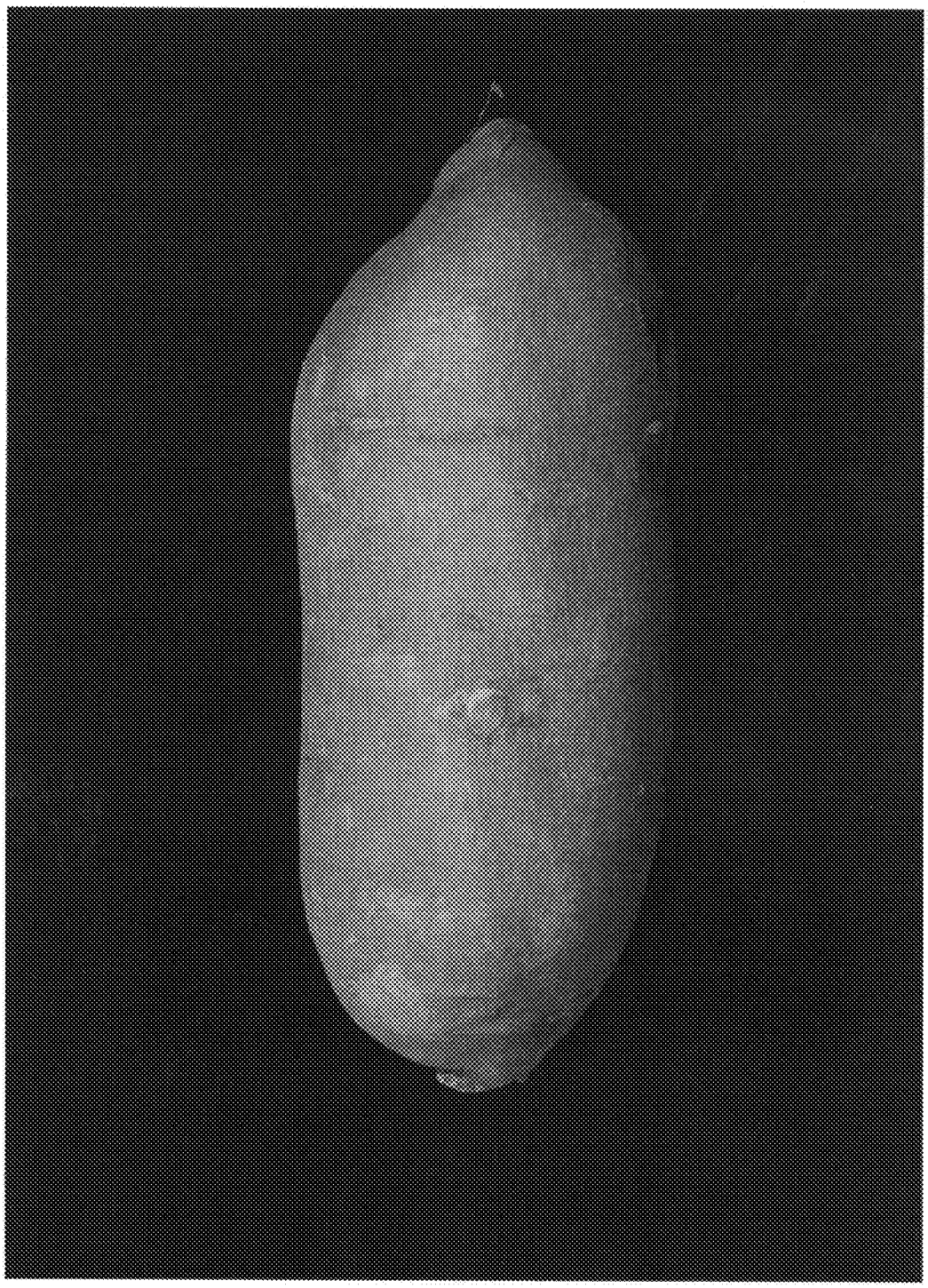
FIG. 1 is a color photograph of the fleshy root form of the novel variety of sweetpotato identified as '07-146'.
Figure 2:
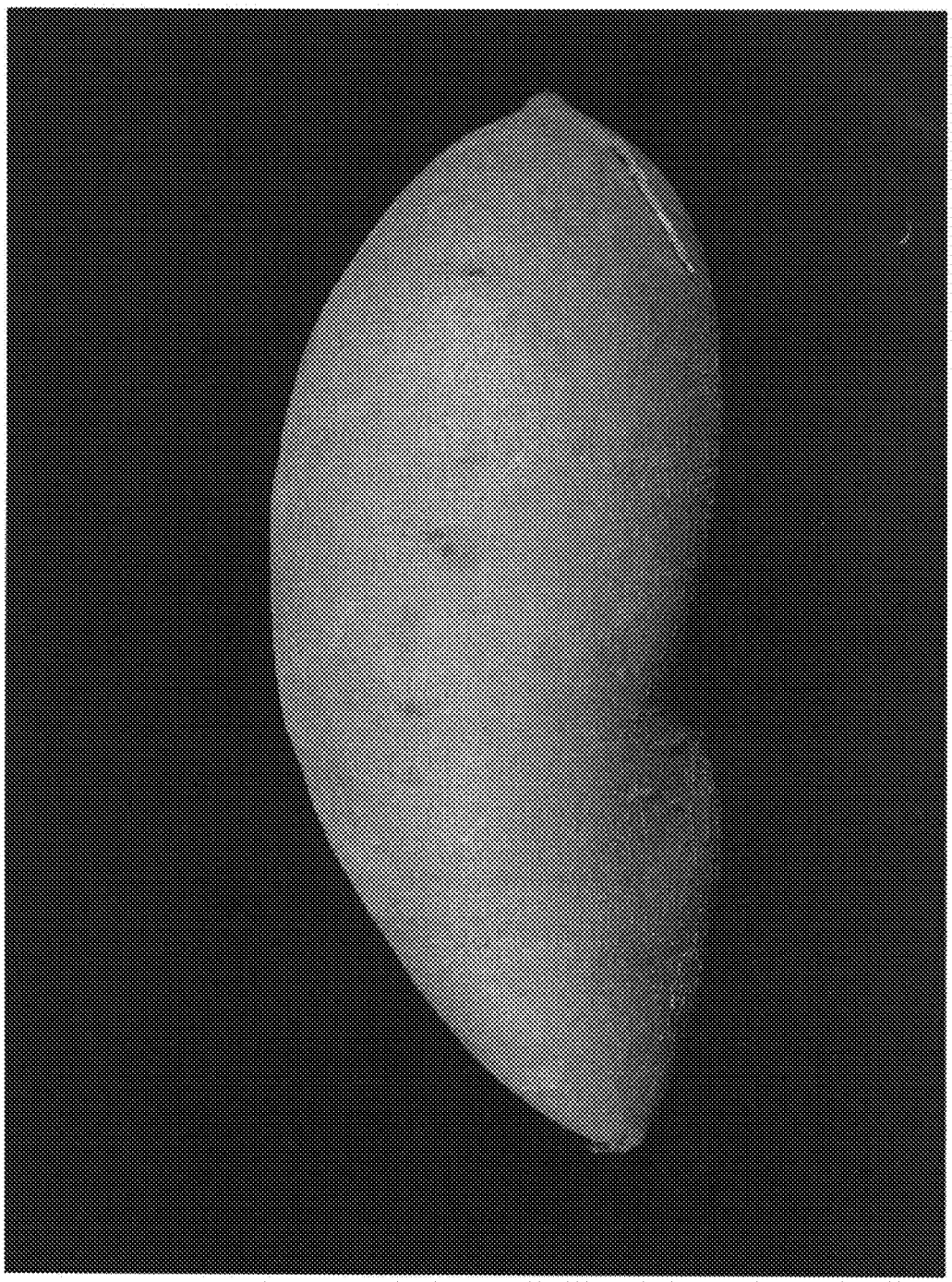
FIG. 2 is a color photograph of the fleshy root form of the sweetpotato variety identified as 'Beauregard'.

FIG. 1 depicts the fleshy root form of the '07-146' sweetpotato. The skin is red and differs from the light to medium rose, 'Beauregard', both at harvest and after several months of storage as shown in Table 1. MUNSELL® Book of Color values for skin and flesh for both '07-146' and 'Beauregard' storage roots 5 days after harvest are shown in Table 1. The 'Beauregard' sweetpotato is depicted in FIG. 2. The skin for both '07-146' and 'Beauregard' was smooth. '07-146' storage roots were elliptical with slight lobing, and tend to be more blunt than 'Beauregard'. The '07-146' cortex was 4 mm in depth. The flesh of '07-146' is deep orange compared to the lighter flesh of 'Beauregard'.

TABLE 1

| Variable | Variety | Color |
|---|---|---|
| Skin | '07-146' | 2.5 R (red) 5/6 |
| | 'Beauregard' | 10 R (red) 6/6 |
| Flesh | '07-146' | 2.5 Y (yellow) R (red) 7/12 |
| | 'Beauregard' | 2.5 Y (yellow) R (red) 7/10 |

Figure 3:
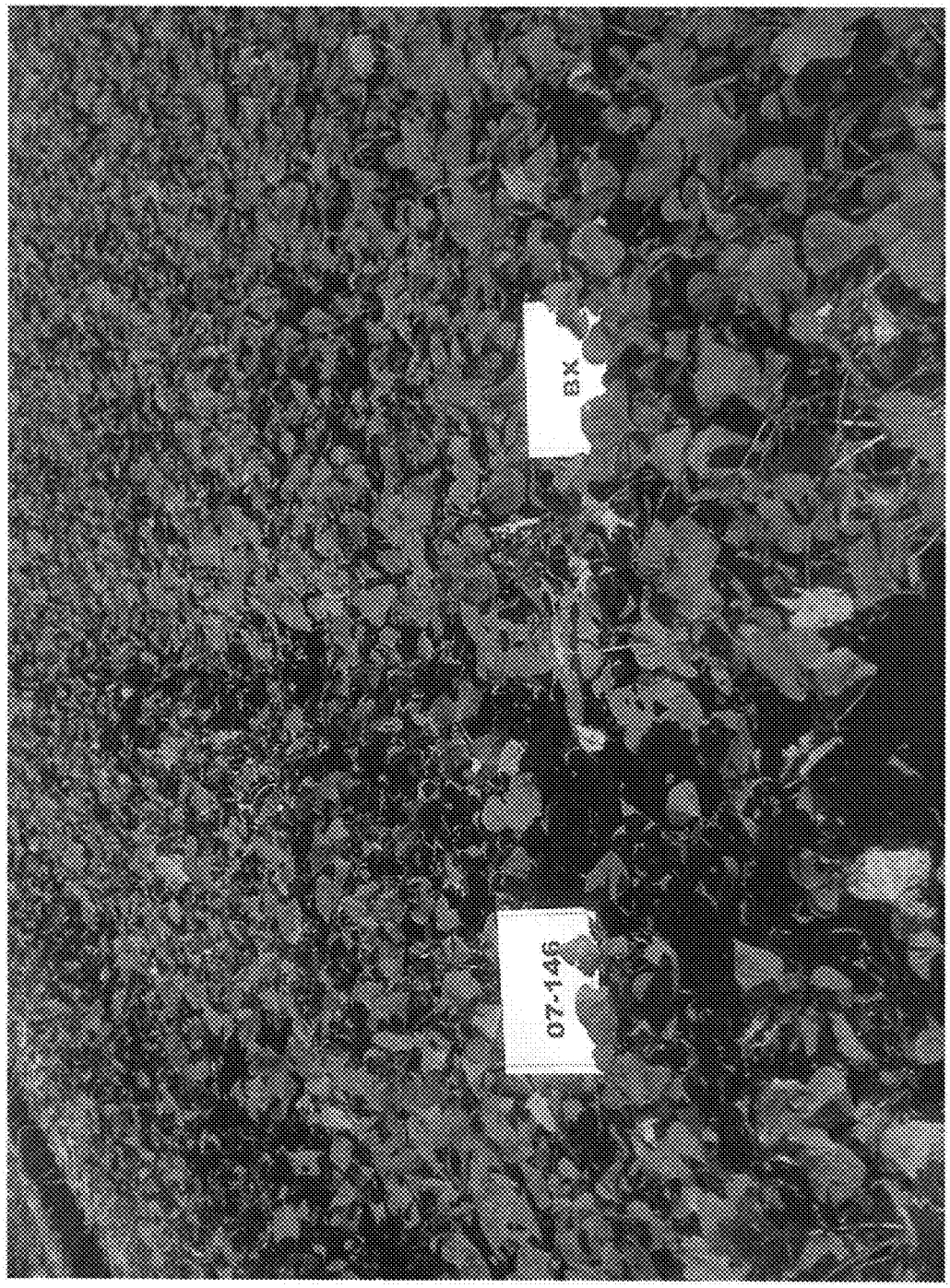
FIG. 3 is a color photograph of the canopy biomasses of the variety of sweetpotato identified as 'Beauregard' (shown on the right side of the photograph) and the novel variety identified as '07-146' (shown on the left side of the photograph).

FIG. 3 depicts the canopy biomass of both '07-146' sweetpotatoes and 'Beauregard' sweetpotatoes. '07-146' has green-stemmed vines [5 G (green) Y (yellow) (7/8)] from the apex to the crown of the roots. The '07-146' canopy biomass is slightly more compact, but appears similar to 'Beauregard'. The '07-146' canopy architecture was 33 cm in height from the soil surface and 335 cm in a radial spread. For '07-146', three to four main vines arose from the main stem near the soil surface. The stem giving rise to these vines was 1.7-1.9 cm in diameter; the 5-6 lateral vines were 180 cm in length with diameters of about 0.7-0.9 cm at 65 cm from the base, diameters of about 1 cm at the base of the vine, and diameters of about 0.6 cm at the first internode of the first fully developed leaf from the apex. Five to six lateral branches arose from each of the main vines. At the first internode from the apex, the internode length was about 3.9 cm between the first and second fully developed leaves. Internode lengths for other sections of the vine averaged about 5.3 cm. Unfolded immature leaves were dark green [5 G (green) Y (yellow) (4/4)] for the upper and lower surface [5 G (green) Y (yellow) (4/4)], which change gradually over one to two nodes from the apex to a green upper surface [5 G (green) Y (yellow) (5/6)] to a green lower surface [5 G (green) Y (yellow) (6/6)]. Mature leaves at five nodes from the apex had an acute apex and mostly a cordate base and a smooth leaf margin. Mature leaves were about 10.9 cm long and 10.9 cm wide. Abaxial veins were green [7.5 G (green) Y (yellow) (6/6)] and red adaxial veins [2.5 R (red)]. The petiole was green [5 G (green) Y (yellow) (7/8)] and similar to the vine. A red [2.5 R (red)] marking was at the base of the leaf junction with the petiole. This coloration is faded but present in major adaxial veins in immature leaves, while diminished in mature leaves. The petiole was 9 cm long at five nodes from the apex, and 3 mm in diameter at 5 cm from the leaf junction. The dormant nodal meristem also was green [5 G (green) Y (yellow) (7/8)].

A typical inflorescence of '07-146' displayed three to four clusters of two to three flowers per peduncle. Peduncles were green [5 G (green) Y (yellow) (7/8)], about 11-13 cm long, and about 4 mm in diameter. Individual flowers were about 4 cm long from the base of the calyx, and the corolla was 4 to 5 cm wide at the opening. The fused flower petals formed a pentagonal pattern with smooth edges. The inner throat of the corolla appeared purple [2.5 R (red) P (purple) (3/6)]. The inner and outer limbs of the corolla (corollas outermost area, distal from the calyx) were very light purple [2.5 R (red) P (purple) (6/4)]. The five sepals comprising the calyx were elliptic with a cordate apex and appeared to be green [2.5 G (green) Y (yellow) (7/8)]; three of these sepals were about 13 mm long and 6 mm wide. Two other sepals (interspersed) were about 10 mm long and 3 mm wide. Sepal margins were smooth. Stigmata were about 1.5 cm long and appeared to be light purple [2.5 R (red) P (purple) (6/4)]. Three of the five stamens were inferior to stigmata. A slight fragrance was present.

EXAMPLE 1

Tests Conducted

To confirm that '07-146' was a new variety, controlled tests (e.g., pathogen responses and yield) were conducted in Baton Rouge, La. 'Beauregard' was selected for comparison because of its importance in commercial United States orange flesh sweetpotato acreage. Diseases that commonly affect the growth of sweetpotatoes were selected to test for pathogen responses in both varieties. Scions of '07-146' and 'Beauregard' reacted similarly to most diseases evaluated in the controlled tests. '07-146' and 'Beauregard' were intermediate to resistant for *Streptomyces* soil rot caused by *Streptomyces ipomoeae* (Person & W. J. Martin) Waksman & Henrici. '07-146' and 'Beauregard' were resistant to *Fusarium* wilt or stem rot caused by *Fusarium oxysporum* Schlect. f. sp. *batatas* (Wollenw.) Snyd. & Hans.

Nematode reproduction was measured in greenhouse tests. '07-146' was intermediate and 'Beauregard' was susceptible to southern root-knot nematode, *Meloidogyne incognita* (Kofoid & White 1919) Chitwood 1949. '07-146' was highly resistant and 'Beauregard' resistant to *Rhizopus* soft rot caused by *Rhizopus stolonifer* (Ehr. ex. Fr.) Lind. Susceptibility to bacterial root rot caused by *Dickeya dadantii* Samson et al. was measured by postharvest inoculation of storage roots. '07-146' and 'Beauregard' were both susceptible to bacterial root rot.

'07-146' did not appear to show any novel insect resistance.

To determine yield production, complete-block trials using four replications of '07-146' and 'Beauregard' each were conducted in 2009 and 2011 in areas of Louisiana, Mississippi, Arkansas, and Alabama likely to produce '07-146'. '07-146' and 'Beauregard' sweetpotato plants were transplanted in randomized complete-block trials at 31 cm spacings. Each block/plot was fertilized with approximately 250 pounds per acre of a mixed fertilizer comprising 13% N, 13% $P_2O_5$, and 13% $K_2O$. '07-146' was compared to 'Beauregard' at transplanting dates beginning in May-July. Average yields were measured for the following grades of roots: U.S. #1 (51-89 mm in diameter, 76-229 mm long); Canner (25-51 mm in diameter, 51-178 mm long); and Jumbo (larger than U.S. #1 in diameter, length or both, and without objectionable defects). A typical marketable root of '07-146' was 180-190 mm long, 65-80 mm in diameter, with mostly round-elliptic in shapes. The base or distal end tended to be more elongated in comparison to slightly rounder apex (proximal end). U.S. #1 roots typically weighed 150-190 g.

A mid-season transplanting date trial was conducted at Bellefontaine, Miss. in 2009. '07-146' and 'Beauregard' were transplanted on Jun. 3, 2009, and harvested on Oct. 8, 2009 (127 days after planting). Average yields, measured as Metric Tons per Hectare ($MT \cdot ha^{-1}$), are shown in Table 2.

TABLE 2

| Selection | US#1† | Canners† | Jumbos† | TMY‡† |
|---|---|---|---|---|
| '07-146' | 27.2a | 30.5a | 3.0a | 63.5a |
| 'Beauregard' | 16.0a | 22.8a | 3.1a | 43.1a |

†Average yields in $MT \cdot ha^{-1}$ of varieties followed by a common letter do not differ significantly ($P < 0.05$) according to Duncan's Multiple Range Test.
TMY‡ = total marketable yield An early-season transplanting date trial was also conducted at Ville Platte, La. on May 27, 2009, and harvested on Sep. 30, 2009 (126 days after planting). Average yields ($MT \cdot ha^{-1}$) by grade of '07-146' and 'Beauregard' are shown in Table 3.

TABLE 3

| Selection | US#1† | Canners† | Jumbos† | TMY‡† |
|---|---|---|---|---|
| '07-146' | 38.3a | 6.4a | 0a | 44.8a |
| 'Beauregard' | 32.9a | 6.1a | 4.4a | 43.3b |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Bonita, La. on Jun. 2, 2010, and harvested on Sep. 30, 2010 (120 days after planting). Average yields ($MT \cdot ha^{-1}$) by grade of '07-146' and 'Beauregard' are shown in Table 4.

TABLE 4

| Selection | US#1† | Canners† | Jumbos† | TMY‡† |
|---|---|---|---|---|
| '07-146' | 22.1a | 8.4a | 9.7a | 40.3a |
| 'Beauregard' | 14.4a | 7.7a | 10.8a | 32.9a |

†Average yields in $MT \cdot ha^{-1}$ of varieties followed by a common letter do not differ significantly ($P < 0.05$) according to Duncan's Multiple Range Test.
TMY‡ = total marketable yield A late-season transplanting date trial was also conducted at Oak Grove, La. on Jul. 8 , 2010, and harvested on Nov. 10, 2010 (125 days after planting). Average yields ($MT \cdot ha^{-1}$) by grade of '07-146' and 'Beauregard' are shown in Table 5.

TABLE 5

| Selection | US#1† | Canners† | Jumbos† | TMY‡† |
|---|---|---|---|---|
| '07-146' | 20.5a | 2.3a | 0.2a | 23.1a |
| 'Beauregard' | 8.6b | 6.1a | 1.1a | 15.9b |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Montrose, Ark. on Jun. 2, 2010, and harvested on Oct. 15, 2010 (135 days after planting). Average yields ($MT \cdot ha^{-1}$) by grade of '07-146' and 'Beauregard' are shown in Table 6.

TABLE 6

| Selection | US#1† | Canners† | Jumbos† | TMY‡† |
|---|---|---|---|---|
| '07-146' | 17.2a | 12.2a | 6.8a | 36.1a |
| 'Beauregard' | 7.7b | 15.5a | 4.0a | 27.2a |

†Average yields in $MT \cdot ha^{-1}$ of varieties followed by a common letter do not differ significantly ($P < 0.05$) according to Duncan's Multiple Range Test.
TMY‡ = total marketable yield As shown in Tables 2-6, '07-146' produced yields comparable to, and mostly exceeding 'Beauregard' in regional trials at various planting dates. Yield in comparison to 'Beauregard' in heavier silt loam soils (Tables 3 and 5) were similar to outcomes in lighter, sandy loam soils (Tables 2, 4 and 6). Replicated plots at other farms and on station have shown '07-146' has consistent yields for early, middle, or late season plantings. Yield declines are within norms in poor environments. '07-146' had harvestable roots approximately 115-120 days after planting, which is typical development time for sweetpotatoes and comparable to 'Beauregard'. The yield of Jumbo grade is indicative of earliness and '07-146' was similar to the jumbo yield of 'Beauregard' statistically; however, rank changed from plot to plot. Yield in 13 other plots (data not shown) in Louisiana in years 2009 and 2010 showed no significant difference in yield in comparison to the 'Beauregard' variety for the important U.S. #1 grade in 9 plots. Yield of '07-146' for U.S. #1 grade was significantly higher in 4 plots in comparison to 'Beauregard'. In total, '07-146' ranked higher in yield of U.S. #1 grade in 12 out of 13 farm plots in comparison to 'Beauregard'. These same trends were found for total marketable yield and reflect on an increase in storage roots in all classes. Field observations suggest that '07-146' has more tolerance to saturated soil conditions in comparison to 'Beauregard'; however, more trials are needed.

Sugar profiles for baked '07-146' and 'Beauregard' are shown in Table 7. For this 2011 test, roots were stored for six months after which they were baked at 190° C. for approximately 2.0 h. Sucrose content in baked '07-146' is higher in comparison to baked 'Beauregard'. Total sugar content was similar. Dry matter is similar for '07-146' and 'Beauregard' at 23% in freshly harvested roots. These results demonstrate a similar level of moistness for '07-146' and 'Beauregard' and enhanced sweetness for '07-146'.

TABLE 7

| Selection | Fructose‡ | Glucose‡ | Sucrose‡ | Maltose‡ | Total sugars†‡ |
|---|---|---|---|---|---|
| '07-146' | 1.64 | 3.05 | 6.01 | 3.90 | 14.60 |
| 'Beauregard' | 1.14 | 1.71 | 4.20 | 6.71 | 13.77 |

†Total sugars = fructose + glucose + maltose + sucrose.
‡$mg \cdot g^{-1}$ fresh weight basis.

'07-146' should be a valuable commercial sweetpotato variety. '07-146' produced plants (sprouts) comparable to 'Beauregard'. Days to harvest for '07-146' were similar to 'Beauregard'. '07-146' exhibited increased sucrose content in comparison to 'Beauregard'. '07-146' has exhibited superior yield in plantings in comparison to 'Beauregard'.

We claim:

1. A new and distinct variety of *Ipomoea batatas* plant named '07-146' as described and illustrated in the specification herein.

* * * * *